United States Patent

Maurer et al.

[11] 4,078,057
[45] Mar. 7, 1978

[54] O-ALKYL-O-(1-CARBALKOXY-2-TERT.-PENTYRYL-VINYL)-(THIONO) (THIOL) PHOSPHORIC (PHOSPHONIC) ACID ESTERS, ESTER-AMIDES AND METHOD OF COMBATTING INSECTS

[75] Inventors: Fritz Maurer; Hans-Jochem Riebel, both of Wuppertal; Bernhard Homeyer, Leverkusen; Wolfgang Behrenz, Overath; Ingeborg Hammann, Cologne; Wilhelm Stendel, Wuppertal, all of Germany

[73] Assignee: Bayer Aktiengesellschaft, Leverkusen, Germany

[21] Appl. No.: 729,931

[22] Filed: Oct. 6, 1976

[30] Foreign Application Priority Data

Oct. 23, 1975 Germany .............................. 2547513

[51] Int. Cl.² ........................ A01N 9/36; C07F 9/165; C07F 9/38
[52] U.S. Cl. ..................................... 424/212; 260/941
[58] Field of Search ........................ 260/941; 424/212

[56] References Cited

U.S. PATENT DOCUMENTS 3,644,601  2/1972  Miller et al. .......................... 260/941
3,733,376  5/1973  Kristiansen et al. .................. 424/212

Primary Examiner—Anton H. Sutto
Attorney, Agent, or Firm—Burgess, Dinklage & Sprung

[57] ABSTRACT

O-Alkyl-O-(1-carbalkoxy-2-tert.-pentyryl-vinyl)-(thiono) (thiol) phosphoric (phosphonic) acid esters and esteramides of the formula

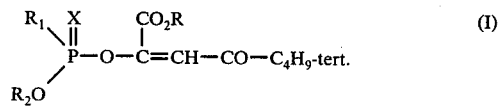

in which
R and $R_2$ each independently is alkyl with 1 to 6 carbon atoms,
$R_1$ is phenyl, or alkyl, alkoxy, alkylthio or alkylamino each with 1 to 6 carbon atoms, and
X is oxygen or sulfur,
which possess insecticidal and acaricidal properties.

10 Claims, No Drawings

O-ALKYL-O-(1-CARBALKOXY-2-TERT.-PENTYRYL-VINYL)-(THIONO) (THIOL) PHOSPHORIC (PHOSPHONIC) ACID ESTERS, ESTER-AMIDES AND METHOD OF COMBATTING INSECTS

The present invention relates to and has for its objects the provision of particular new substituted O-alkyl-O-(1-carbalkoxy-2-tert.-pentyryl-vinyl)-(thiono) (thiol) phosphoric (phosphonic) acid esters and ester-amides which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in German Patent Specification No. 864,252 that O,O-dialkyl-O-(1-oxo-cyclohexenyl)-thionophosphoric acid esters, for example O,O-diisopropyl-O-[1-oxo-2-cyclohexen-(3)yl]-thionophosphoric acid ester (Compound A), possess insecticidal properties.

The present invention provides 1-carbalkoxyvinyl-(thiono) (thiol)phosphoric(phosphonic) acid esters and ester-amides of the formula

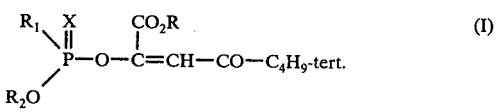

in which
R and $R_2$ each independently is alkyl with 1 to 6 carbon atoms,
$R_1$ is phenyl, or alkyl, alkoxy, alkylthio or alkylamino each with 1 to 6 carbon atoms, and
X is oxygen or sulfur.

Preferably, R and $R_2$ represent straight-chain or branched alkyl with 1 to 4 carbon atoms, and $R_1$ represents straight-chain or branched alkyl or alkoxy with 1 to 3 carbon atoms or straight-chain or branched alkylthio or monoalkylamino with 1 to 4 carbon atoms, or phenyl and X represents sulfur.

The general formula (I) here encompasses the corresponding cis- and trans-isomers of the formula (II) and (III), as well as mixtures of both components:

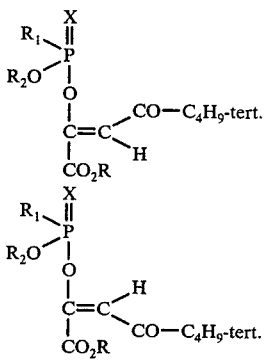

Surprisingly, the 1-carbalkoxyvinyl(thiono) (thiol)-phosphoric(phosphonic) acid esters and ester-amides according to the invention exhibit a better insecticidal and acaricidal action than the corresponding known O,O-dialkyl-O-(1-oxo-cyclohexenyl)-thionophosphoric acid esters of similar structure and of the same type of action. The products according to the present invention thus represent a genuine enrichment of the art.

The invention also provides a process for the preparation of a 1-carbalkoxyvinyl(thiono)(thiol)phosphoric(phosphonic) acid ester or ester-amide of the formula (I) in which a (thiono)(thiol)phosphoric(phosphonic) acid ester halide or ester-amide halide of the formula

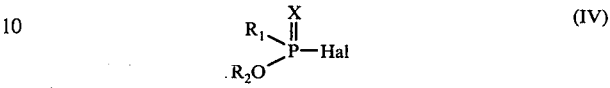

in which
$R_1$, $R_2$ and X have the abovementioned meanings and
Hal represents halogen, preferably chlorine,
is reacted with a tert.-pentyrylpyruvic acid alkyl ester of the formula (V) or its enol form (Va)

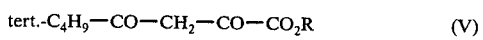

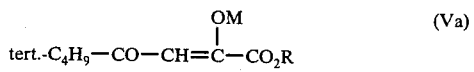

in which
R has the abovementioned meaning and
M represents hydrogen or one equivalent of an alkali metal, alkaline earth metal or ammonium,
optionally in the presence of an acid acceptor, and optionally in the presence of a solvent or diluent.

If, for example, O-iso-propyl-N-ethyl-phosphoric acid ester-amide chloride and tert.-pentyrylpyruvic acid n-propyl ester are used as starting materials, the course of the reaction can be represented by the following formula scheme:

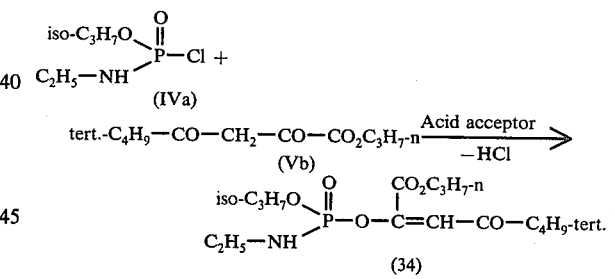

The (thiono)(thiol)phosphoric(phosphonic) acid ester halides and ester-amide halides (IV) required as starting materials are known and can be prepared in accordance with customary processes.

The following may be mentioned as individual examples of starting materials: O,O-dimethyl-, O,O-diethyl-, O,O-di-n-propyl-, O,O-di-iso-propyl-, O-methyl-O-ethyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-sec.-butyl- and O-n-propyl-O-iso-butyl-phosphoric acid diester chloride and the corresponding thiono analogues, and O,S-dimethyl-, O,S-diethyl-, O,S-di-n-propyl-, O,S-di-iso-propyl-, O,S-di-n-butyl-, O,S-di-iso-butyl-, O,S-di-tert.-butyl-, O-ethyl-S-n-propyl, O-ethyl-S-iso-propyl, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethylthiol-phosphoric acid diester halides and the corresponding thiono analogues, and also O-methyl-N-methyl-, O-methyl-N-ethyl-, O-methyl-N-n-propyl-, O- methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl, O-iso-propyl-N-isopropyl-, O-n-butyl-N-methyl-, O-n-butyl-N-ethyl-, O-n-butyl-N-n-propyl-, O-n-buty-N-iso-propyl-, O-tert.-butyl-N-methyl-, O-tert.-butyl-N-ethyl-, O-tert.-butyl-N-n-propyl-, O-tert.-butyl-N-iso-propyl-, O-iso-butyl-N-methyl-, O-iso-butyl-N-ethyl-, O-sec.-butyl-N-methyl-and O-sec.-butyl-N-ethyl-phosphoric acid ester amide chloride and the corresponding thiono analogues, as well as O-methyl-, O-ethyl-, O-n-propyl-, O-iso-propyl-, O-n-butyl-, O-iso-butyl-, O-sec.-butyl- and O-tert.-butyl-methane-, -ethane-, -n-propane-, -iso-propane- and -phenyl-phosphonic acid ester chloride and the corresponding thiono analogues.

The tert.-pentyrylpyruvic acid alkyl esters (V) and (Va) can be prepared by condensation of pincacoline with oxalic acid dialkyl esters, if appropriate in the presence of an alcoholate, for example potassium tert.-butylate.

The following may be mentioned as individual examples of such esters: tert.-pentyrylpyruvic acid methyl ester, ethyl ester, n-propyl ester, iso-propyl ester, n-butyl ester, isobutyl ester and sec.-butyl ester.

The reaction according to the invention is preferably carried out in the presence of a solvent or diluent. Practically all inert organic solvents can be used for this purpose. They include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methy isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamineand pyridine.

The reaction temperature can be varied within a substantial range. In general, the reaction is carried out at 0° to 120° C, preferably at 25° to 60° C.

In general, the reaction is allowed to take place under normal pressure.

In carrying out the process, the starting materials are preferably employed in equimolar amounts. An excess of one or other component produces no significant advantages. In general, the pyruvic acid derivative (V) together with the acid acceptor are first introduced into a solvent and the phoshoric acid component (IV) is added dropwise to this mixture. After completion of the reaction, the batch is poured into an organic solvent, for example toluene, and the organic phase is then worked up in the usual manner by washing, drying and distilling off the solvent.

The new compounds are generally obtained in the form of oils, which in some cases cannot be distilled without decomposition, but are freed from the last volatile constituents by so-called "slight distillation", that is to say by prolonged heating under reduced pressure to moderately elevated temperatures, and they can be purified in this way. They are characterized by the refractive index.

As already mentioned, the 1-carbalkoxyvinyl(thiono)(thiol) phosphoric(phosphonic) acid esters and ester-amides according to the invention are distinguished by an excellent insecticidal and acaricidal activity. They are not only active against plant pests, hygiene pests and pests of stored products, but also, in the veterinary medicine field, against animal parasites (ectoparasites), such as parasitic fly larvae. They combine a low phytotoxicity with a good action against both sucking and biting insects and mites; some compounds also show a development-inhibiting action.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating animal pests, especially insects and arachnida which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example *Blaniulus guttulatus.* From the order of the Chilopoda, for example *Geophilus carpophagus* and Scutigera spec. From the order of the Symphyla, for example, *Scutigerella imaculata.* From the order of the Thysanura, for example, *Lepisma saccharina.* From the order of the Collembola, for example *Onychiurus armatus.* From the order of the Orthoptera, for example, *Blatta orientalis, Periplaneta americana, Leucophaea maderae, Blattella germanica, Acheta domesticus,* Gryllotalpa spp., *Locustra migratoria migratorioides, Melanoplus differentialis* and *Schistocerca gretaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhospalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp, and Psylla spp. From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia Kuhniella, Galleria mellonella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamemsis,* Anthonomus spp., *Sitophilus spp., Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus holoeucus, Gibbium psylloides,* Tribolium spp., *Tenebrio molitor,* Agriotes spp., Conoderus spp., *Melolontha mololontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp, Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limiting, by the following examples:

EXAMPLE 1

Critical concentration test/soil insects I
Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the Table 1 which follows:

Table 1

| Critical concentration test/soil insects I | |
|---|---|
| Active compound | Degree of destruction in % at an active compound concentration of 5 ppm |
| $\begin{array}{c}O\\\parallel\\\text{cyclohexenyl}-O-\overset{S}{\underset{\parallel}{P}}(OC_3H_7\text{-iso})_2\end{array}$ (known) (A) | 0 |
| $(CH_3)_3C-CO-CH=C\begin{array}{c}CO-OC_3H_7\text{-iso}\\\diagdown\\\phantom{xx}\diagup\end{array}\begin{array}{c}S\\\parallel\\O-P\end{array}\begin{array}{c}OC_2H_5\\\diagdown\\C_2H_5\end{array}$ (3) | 100 |
| $(CH_3)_3C-CO-CH=C\begin{array}{c}CO-OC_3H_7\text{-iso}\\\diagdown\\\phantom{xx}\diagup\end{array}\begin{array}{c}S\\\parallel\\O-P\end{array}\begin{array}{c}OC_2H_5\\\diagdown\\OC_3H_7\text{-n}\end{array}$ (6) | 100 |
| $(CH_3)_3C-CO-CH=C\begin{array}{c}CO-OC_2H_5\\\diagdown\\\phantom{xx}\diagup\end{array}\begin{array}{c}S\\\parallel\\O-P(OC_2H_5)_2\end{array}$ (1) | 100 |
| $(CH_3)_3C-CO-CH=C\begin{array}{c}CO-OC_2H_5\\\diagdown\\\phantom{xx}\diagup\end{array}\begin{array}{c}S\\\parallel\\O-P\end{array}\begin{array}{c}OC_2H_5\\\diagdown\\OC_3H_7\text{-n}\end{array}$ (9) | 100 |
| $(CH_3)_3C-CO-CH=C\begin{array}{c}CO-OC_2H_5\\\diagdown\\\phantom{xx}\diagup\end{array}\begin{array}{c}S\\\parallel\\O-P\end{array}\begin{array}{c}CH_3\\\diagdown\\O-C_3H_7\text{-iso}\end{array}$ (16) | 100 |
| $(CH_3)_3C-CO-CH=C\begin{array}{c}CO-OC_2H_5\\\diagdown\\\phantom{xx}\diagup\end{array}\begin{array}{c}S\\\parallel\\O-P\end{array}\begin{array}{c}OCH_3\\\diagdown\\C_2H_5\end{array}$ (17) | 100 |

EXAMPLE 2

Critical concentration test/soil insects II
Test insect: Phorbia antiqua maggots in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects have been killed and was 0% if exactly as many test insects were still alive as in the case of the untreated control.

The active compounds, amounts used and results can be seen from the Table 2 which follows:

Table 2

Critical concentration test/soil insects II

| Active compound | Degree of destruction in % at an active compound concentration of 2.5 ppm |
|---|---|
| (A) cyclohexenyl-O-P(=S)(OC$_3$H$_7$-iso)$_2$ (known) | 0 |
| (2) (CH$_3$)$_3$C—CO—CH=C(CO—OC$_3$H$_7$-iso)(O—P(=S)(OC$_2$H$_5$)$_2$) | 100 |
| (3) (CH$_3$)$_3$C—CO—CH=C(CO—OC$_3$H$_7$-iso)(O—P(=S)(OC$_2$H$_5$)(C$_2$H$_5$)) | 100 |
| (6) (CH$_3$)$_3$C—CO—CH=C(CO—OC$_3$H$_7$-iso)(O—P(=S)(OC$_2$H$_5$)(OC$_3$H$_7$-n)) | 100 |
| (1) (CH$_3$)$_3$C—CO—CH=C(CO—OC$_2$H$_5$)(O—P(=S)(OC$_2$H$_5$)(C$_2$H$_5$)) | 100 |
| (16) (CH$_3$)$_3$C—CO—CH=C(CO—OC$_2$H$_5$)(O—P(=S)(CH$_3$)(O—C$_3$H$_7$-iso)) | 100 |

EXAMPLE 3

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm$^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following Table 3:

Table 3

(*Drosophila* test)

| Active compounds | Active compound concentration in % | Degree of destruction in % after 1 day |
|---|---|---|
| (A) cyclohexenyl-O-P(=S)(O—C$_3$H$_7$-iso)$_2$ (known) | 0.01 / 0.001 | 98 / 0 |
| (12) (CH$_3$)$_3$C—CO—CH=C(CO—OCH$_3$)(O—P(=S)(OC$_2$H$_5$)$_2$) | 0.01 / 0.001 | 100 / 100 |
| (13) (CH$_3$)$_3$C—CO—CH=C(CO—OCH$_3$)(O—P(=S)(OC$_2$H$_5$)(C$_2$H$_5$)) | 0.01 / 0.001 | 100 / 100 |
| (15) (CH$_3$)$_3$C—CO—CH=C(CO—OC$_2$H$_5$)(O—P(=S)(OCH$_3$)$_2$) | 0.01 / 0.001 | 100 / 100 |
| (17) (CH$_3$)$_3$C—CO—CH=C(CO—OC$_2$H$_5$)(O—P(=S)(OCH$_3$)(C$_2$H$_5$)) | 0.01 / 0.001 | 100 / 100 |

Table 3-continued
(Drosophila test)

| Active compounds | Active compound concentration in % | Degree of destruction in % after 1 day |
|---|---|---|
| $(CH_3)_3C-CO-CH=C \begin{smallmatrix} CO-OC_2H_5 \\ O-P(S)(O-C_3H_7\text{-iso})(CH_3) \end{smallmatrix}$ (16) | 0.01<br>0.001 | 100<br>100 |
| $(CH_3)_3C-CO-CH=C \begin{smallmatrix} CO-OC_2H_5 \\ O-P(S)(OC_2H_5)_2 \end{smallmatrix}$ (1) | 0.01<br>0.001 | 100<br>100 |
| $(CH_3)_3C-CO-CH=C \begin{smallmatrix} CO-OC_2H_5 \\ O-P(S)(OC_2H_5)(C_2H_5) \end{smallmatrix}$ (8) | 0.01<br>0.001 | 100<br>100 |
| $(CH_3)_3C-CO-CH=C \begin{smallmatrix} CO-OC_3H_7\text{-iso} \\ O-P(S)(OC_2H_5)_2 \end{smallmatrix}$ (2) | 0.01<br>0.001 | 100<br>100 |
| $(CH_3)_3C-CO-CH=C \begin{smallmatrix} CO-OC_3H_7\text{-iso} \\ O-P(S)(OC_2H_5)(C_2H_5) \end{smallmatrix}$ (3) | 0.01<br>0.001 | 100<br>100 |

EXAMPLE 4

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 4:

Table 4
(Plutella test)

| Active compounds | Active compound concentration in % | Degree of destruction in % after 3 days |
|---|---|---|
| 3-oxo-cyclohex-1-enyl $O-P(S)(OC_3H_7\text{-iso})_2$ (known) (A) | 0.1 | 0 |
| $(CH_3)_3C-CO-CH=C \begin{smallmatrix} CO-OCH_3 \\ O-P(S)(OC_2H_5)_2 \end{smallmatrix}$ (12) | 0.1 | 100 |
| $(CH_3)_3C-CO-CH=C \begin{smallmatrix} CO-OCH_3 \\ O-P(S)(OC_2H_5)(C_2H_5) \end{smallmatrix}$ (13) | 0.1 | 100 |
| $(CH_3)_3C-CO-CH=C \begin{smallmatrix} CO-OC_2H_5 \\ O-P(S)(C_2H_5)_2 \end{smallmatrix}$ (1) | 0.1 | 100 |
| $(CH_3)_3C-CO-CH=C \begin{smallmatrix} CO-OC_2H_5 \\ O-P(S)(OCH_3)(OC_3H_7\text{-n}) \end{smallmatrix}$ (10) | 0.1 | 100 |
| $(CH_3)_3C-CO-CH=C \begin{smallmatrix} CO-OC_2H_5 \\ O-P(S)(OC_2H_5)(OC_3H_7\text{-n}) \end{smallmatrix}$ (9) | 0.1 | 100 |
| $(CH_3)_3C-CO-CH=C \begin{smallmatrix} CO-OC_2H_5 \\ O-P(S)(OCH_3)(C_2H_5) \end{smallmatrix}$ (17) | 0.1 | 100 |
| $(CH_3)_3C-CO-CH=C \begin{smallmatrix} CO-OC_2H_5 \\ O-P(S)(OC_2H_5)(C_2H_5) \end{smallmatrix}$ (8) | 0.1 | 100 |
| $(CH_3)_3C-CO-CH=C \begin{smallmatrix} CO-OC_2H_5 \\ O-P(S)(OC_3H_7\text{-iso})(CH_3) \end{smallmatrix}$ (16) | 0.1 | 100 |
| $(CH_3)_3C-CO-CH=C \begin{smallmatrix} CO-OC_3H_7\text{-iso} \\ O-P(S)(OC_2H_5)_2 \end{smallmatrix}$ (2) | 0.1 | 100 |
| $(CH_3)_3C-CO-CH=C \begin{smallmatrix} CO-OC_3H_7\text{-iso} \\ O-P(S)(OC_2H_5)(C_2H_5) \end{smallmatrix}$ (3) | 0.1 | 100 |
| $(CH_3)_3C-CO-CH=C \begin{smallmatrix} CO-OC_3H_7\text{-iso} \\ O-P(S)(OC_2H_5)(OC_3H_7\text{-n}) \end{smallmatrix}$ (6) | 0.1 | 100 |

EXAMPLE 5

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 5:

Table 5
(Myzus test)

| Active compound | Active compound concentration in % | Degree of destruction in % after 3 days |
|---|---|---|
| 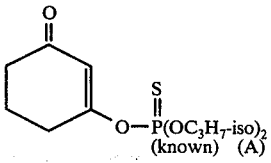 (known) (A) | 0.1<br>0.01 | 95<br>0 |
| $(CH_3)_3C-CO-CH=C\langle_{O-P(OC_2H_5)_2}^{CO-OCH_3\;\;\;S}$ (12) | 0.1<br>0.01 | 100<br>95 |
| $(CH_3)_3C-CO-CH=C\langle_{O-P(OC_2H_5)(C_2H_5)}^{CO-OCH_3\;\;\;S}$ (13) | 0.1<br>0.01 | 100<br>95 |
| $(CH_3)_3C-CO-CH=C\langle_{O-P(OCH_3)(C_2H_5)}^{CO-OC_2H_5\;\;\;S}$ (17) | 0.1<br>0.01 | 100<br>99 |
| $(CH_3)_3C-CO-CH=C\langle_{O-P(OC_3H_7\text{-iso})(CH_3)}^{CO-OC_2H_5\;\;\;S}$ (16) | 0.1<br>0.01 | 100<br>100 |
| $(CH_3)_3C-CO-CH=C\langle_{O-P(OC_2H_5)_2}^{CO-OC_2H_5\;\;\;S}$ (1) | 0.1<br>0.01 | 100<br>100 |
| $(CH_3)_3C-CO-CH=C\langle_{O-P(OC_2H_5)(C_2H_5)}^{CO-OC_2H_5\;\;\;S}$ (8) | 0.1<br>0.01 | 100<br>100 |
| $(CH_3)_3C-CO-CH=C\langle_{O-P(OC_2H_5)_2}^{CO-OC_3H_7\text{-iso}\;\;\;S}$ (2) | 0.1<br>0.01 | 100<br>100 |
| $(CH_3)_3C-CO-CH=C\langle_{O-P(OC_2H_5)_2}^{CO-OC_3H_7\text{-iso}\;\;\;O}$ (7) | 0.1<br>0.01 | 100<br>100 |
| $(CH_3)_3C-CO-CH=C\langle_{O-P(OC_2H_5)(C_2H_5)}^{CO-OC_3H_7\text{-iso}\;\;\;S}$ (3) | 0.1<br>0.01 | 100<br>100 |

Table 5-continued (Myzus test)

| Active compound | Active compound concentration in % | Degree of destruction in % after 3 days |
|---|---|---|
| (CH$_3$)$_3$C—CO—CH=C(CO—OC$_3$H$_7$-iso)(O—P(=S)(OC$_2$H$_5$)(OC$_3$H$_7$-n)) (6) | 0.1<br>0.01 | 100<br>100 |
| (CH$_3$)$_3$C—CO—CH=C(CO—OC$_3$H$_7$-iso)(O—P(=S)(OC$_2$H$_5$)(SC$_3$H$_7$-n)) (5) | 0.1<br>0.01 | 100<br>95 |
| (CH$_3$)$_3$C—CO—CH=C(CO—OC$_3$H$_7$-iso)(O—P(=S)(OC$_2$H$_5$)(NH—C$_3$H$_7$-iso)) (4) | 0.1<br>0.01 | 100<br>100 |

EXAMPLE 6

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 6:

Table 6

(Tetranychus test/resistant)

| Active compound | Active compound concentration in % | Degree of destruction in % after 2 days |
|---|---|---|
| cyclohexenone—O—P(=S)(OC$_3$H$_7$-iso)$_2$ (known) (A) | 0.1 | 0 |
| (CH$_3$)$_3$C—CO—CH=C(CO—OC$_2$H$_5$)(O—P(=S)(OC$_3$H$_7$-iso)(CH$_3$)) (16) | 0.1 | 75 |
| (CH$_3$)$_3$C—CO—CH=C(CO—OC$_3$H$_7$-iso)(O—P(=O)(OC$_2$H$_5$)$_2$) (7) | 0.1 | 70 |
| (CH$_3$)$_3$C—CO—CH=C(CO—OC$_3$H$_7$-iso)(O—P(=S)(OC$_2$H$_5$)(C$_2$H$_5$)) (3) | 0.1 | 70 |
| (CH$_3$)$_3$C—CO—CH=C(CO—OC$_3$H$_7$-iso)(O—P(=S)(OC$_2$H$_5$)(OC$_3$H$_7$-n)) (6) | 0.1 | 70 |

Table 6-continued

(Tetranychus test/resistant)

| Active compound | Active compound concentration in % | Degree of destruction in % after 2 days |
|---|---|---|
| (CH$_3$)$_3$C—CO—CH=C(CO—OC$_3$H$_7$-iso)(O—P(=S)(OC$_2$H$_5$)(SC$_3$H$_7$-n)) (5) | 0.1 | 85 |
| (CH$_3$)$_3$C—CO—CH=C(CO—OC$_3$H$_7$-iso)(O—P(=S)(OC$_2$H$_5$)(NH—C$_3$H$_7$-iso)) (4) | 0.1 | 70 |

EXAMPLE 7

LT$_{100}$ test for Diptera
Test insects: Aedes aegypti
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there is a 100% destruction can be seen from the following Table 7:

Table 7

(LT$_{100}$ test for Diptera/Aedes aegypti)

| Active compounds | Active compound concentration in % | LT$_{100}$ in minutes (') or hours (hrs) |
|---|---|---|
| O=⟨⟩—O—P(=S)(OC$_3$H$_7$-iso)$_2$ (known) (A) | 0.2 | 3 hrs = 0% |
| (CH$_3$)$_3$C—CO—CH=C(CO—OC$_2$H$_5$)(O—P(=S)(OCH$_3$)$_2$) (15) | 0.02 | 3 hrs = 100% |
| (CH$_3$)$_3$C—CO—CH=C(CO—OCH$_3$)(O—P(=S)(OC$_2$H$_5$)$_2$) (12) | 0.02 | 2 hrs = 100% |
| (CH$_3$)$_3$C—CO—CH=C(CO—OC$_2$H$_5$)(O—P(=S)(OC$_2$H$_5$)$_2$) (1) | 0.02 | 3 hrs = 100% |
| (CH$_3$)$_3$C—CO—CH=C(CO—OC$_3$H$_7$-iso)(O—P(=S)(OC$_2$H$_5$)$_2$) (2) | 0.02 | 3 hrs = 100% |

Table 7-continued

(LT$_{100}$ test for Diptera/*Aedes aegypti*)

| Active compounds | Active compound concentration in % | LT$_{100}$ in minutes (') or hours (hrs) |
|---|---|---|
| (CH$_3$)$_3$C—CO—CH=C(CO—OC$_2$H$_5$)(O—P(=S)(OCH$_3$)(OC$_3$H$_7$-n)) (10) | 0.02 | 3 hrs = 90% |
| (CH$_3$)$_3$C—CO—CH=C(CO—OCH$_3$)(O—P(=S)(OC$_2$H$_5$)(C$_2$H$_5$)) (13) | 0.02 | 2 hrs = 100% |
| (CH$_3$)$_3$C—CO—CH=C(CO—OC$_2$H$_5$)(O—P(=S)(OC$_2$H$_5$)(C$_2$H$_5$)) (8) | 0.02 | 2 hrs = 100% |
| (CH$_3$)$_3$C—CO—CH=C(CO—OC$_3$H$_7$-iso)(O—P(=S)(OC$_2$H$_5$)(C$_2$H$_5$)) (3) | 0.02 | 2 hrs = 100% |
| (CH$_3$)$_3$C—CO—CH=C(CO—OC$_3$H$_7$-iso)(O—P(=O)(OC$_2$H$_5$)$_2$) (7) | 0.02 | 3 hrs = 100% |

EXAMPLE 8

Test insects: Sitophilus granarius
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all test insects had been killed; 0% denotes that no test insects had been killed.

The active compounds, the concentrations of the active compounds, the test insects and the results can be seen from the following Table 8:

Table 8

*Sitophilus granarius* test

| Active compound | Active compound concentration of the solution in % | Degree of destruction in % |
|---|---|---|
| O=⟨cyclohexadienone⟩—O—P(=S)(OC$_3$H$_7$-iso)$_2$ (known) (A) | 0.2 | 0 |
| (CH$_3$)$_3$C—CO—CH=C(CO—OCH$_3$)(O—P(=S)(OC$_2$H$_5$)$_2$) (12) | 0.02 | 100 |
| (CH$_3$)$_3$C—CO—CH=C(CO—OC$_2$H$_5$)(O—P(=S)(OC$_2$H$_5$)$_2$) (1) | 0.02 | 60 |

Table 8-continued

Sitophilus granarius test

| Active compound | Active compound concentration of the solution in % | Degree of destruction in % |
|---|---|---|
| (CH₃)₃C—CO—CH=C(CO—OC₃H₇-iso)(O—P(OC₂H₅)₂=S)  (2) | 0.02 | 100 |
| (CH₃)₃C—CO—CH=C(CO—OC₃H₇-iso)(O—P(=S)(OC₂H₅)(OC₃H₇-n))  (6) | 0.02 | 90 |
| (CH₃)₃C—CO—CH=C(CO—OC₂H₅)(O—P(=S)(OC₂H₅)(C₂H₅))  (8) | 0.02 | 100 |
| (CH₃)₃C—CO—CH=C(CO—OC₃H₇-iso)(O—P(=S)(OC₂H₅)(C₂H₅))  (3) | 0.02 | 100 |
| (CH₃)₃C—CO—CH=C(CO—OC₃H₇-iso)(O—P(=S)(OC₂H₅)(SC₃H₇-n))  (5) | 0.02 | 90 |

EXAMPLE 9
Test with parasitic fly larvae

Solvent: 35 parts by weight of ethylene polyglycol monomethyl ether 35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The active compounds investigated, the concentrations of the active compounds used and the results obtained can be seen from Table 9 which follows:

Table 9
(Test with parasitic fly larvae/Lucilia cuprina)

| Active Compound | Active compound concentration in ppm | Degree of destruction in % |
|---|---|---|
| n-C₃H₇O—P(=S)(OC₂H₅)—O—C(CO₂C₃H₇-iso)=CH—CO—C₄H₉-tert.  (6) | 100 | 100 |
|  | 30 | 100 |
|  | 10 | 100 |
| (C₂H₅O)₂P(=S)—O—C(CO₂CH₃)=CH—CO—C₄H₉-tert.  (12) | 100 | 100 |
|  | 20 | 100 |
|  | 10 | 100 |

The following further examples are set forth to illustrate, without limitation, the manner of producing the instant compounds according to the present invention.

EXAMPLE 10

(a) tert.-C₄H₉-CO-CH₂-CO-CO-OC₂H₅ (Vc)

The tert.-pentyrylpyruvic acid ethyl esters of the formulae (V) and (Va) which were required as starting materials were prepared as follows:

A mixture of 292 g (2 mols) of oxalic acid diethyl ester and 200 g (2 moles) of pinacoline were added dropwise to a solution of 224 g (2 moles) of potassium tert.-butylate in 300 ml of ethanol at 20° to 30° C. The reaction mixture was stirred for 5 hours at 60° to 70° C and was then cooled, and the batch was poured into 1 liter of water. The aqueous solution was extracted once with 300 ml of methylene chloride, the extract was discarded, the aqueous phase was then acidified with concentrated hydrochloric acid while cooling with ice and was extracted by shaking twice with 300 ml of toluene, the organic phase was separated off and dried over sodium sulfate the solvent was stripped off under reduced pressure and the residue was distilled. 257 g (64% of theory) of tert.-pentyrylpyruvic acid ethyl ester were obtained as a yellow oil of boiling point 80° C/2 mm Hg and of refractive index $n_D^{23}$: 1.4665.

The following compounds can be synthesized analogously

| Structure | Physical constants | Yield (% of theory) |
|---|---|---|
| tert.—C₄H₉—CO—CH₂—CO—CO—OCH₃  (Vd) | Boiling point₄: 95° C  $n_D^{25}$: 1.4731 | 45 |

-continued

| Structure | Physical constants | Yield (% of theory) |
|---|---|---|
| tert.—$C_4H_9$—CO—CH2—CO—CO—$OC_3H_7$-iso (Ve) | Boiling point$_2$ : 95° C $n_D^{22}$ : 1.4629 | 56 | b)

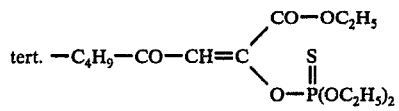 (1)

18.8 g (0.1 mole) of O,O-diethylthionophosphoric acid diester chloride were added dropwise to a mixture of 20 g (0.1 mole) of tert.-pentyrylpyruvic acid ethyl ester and 14.5 g (0.105 mole) of potassium carbonate in 100 ml of acetonitrile at 20° C. The reaction mixture was allowed to react for a further three hours at 40° C and was then poured into 300 ml of toluene. The toluene solution was washed with saturated sodium bicarbonate solution and water and was dried over sodium sulfate. The solvent was then stripped off under reduced pressure and the residue was subjected to "slight distillation". 22 g (62.5% of theory) of O,O-diethyl-O-(1-carbethoxy-2-tert.-pentyryl-vinyl)-thionophosphoric acid ester were obtained in the form of a yellow oil of refractive index $n_D^{26}$: 1.4713.

The following compounds of the formula

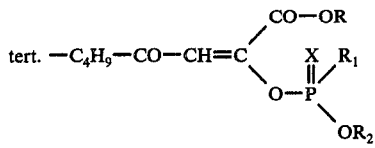 (I)

can be prepared analogously:

Table 10

| Compound No. | X | R | $R_1$ | $R_2$ | Yield (% of theory) | Physical data (refractive index) |
|---|---|---|---|---|---|---|
| 2 | S | —$C_3H_7$-iso | —$OC_2H_5$ | —$C_2H_5$ | 63 | $n_D^{23}$:1.4691 |
| 3 | S | —$C_3H_7$-iso | —$C_2H_5$ | —$C_2H_5$ | 72 | $n_D^{23}$:1.4780 |
| 4 | S | —$C_3H_7$-iso | —NH—$C_3H_7$-iso | —$C_2H_5$ | 53 | $n_D^{23}$:1.4790 |
| 5 | S | —$C_3H_7$-iso | —$SC_3H_7$-n | —$C_2H_5$ | 56 | $n_D^{23}$:1.4945 |
| 6 | S | —$C_3H_7$-iso | —$OC_2H_5$ | —$C_3H_7$-n | 74 | $n_D^{23}$:1.4672 |
| 7 | O | —$C_3H_7$-iso | —$OC_2H_5$ | —$C_2H_5$ | 63 | $n_D^{23}$:1.4489 |
| 8 | S | —$C_2H_5$ | —$C_2H_5$ | —$C_2H_5$ | 81 | $n_D^{23}$:1.4731 |
| 9 | S | —$C_2H_5$ | —$OC_2H_5$ | —$C_3H_7$-n | 60 | $n_D^{26}$:1.4705 |
| 10 | S | —$C_2H_5$ | —$OCH_3$ | —$C_3H_7$-n | 57 | $n_D^{26}$:1.4746 |
| 11 | S | —$C_2H_5$ | —C$_6$H$_5$ | —$C_2H_5$ | 63 | $n_D^{26}$:1.5242 |
| 12 | S | —$CH_3$ | —$OC_2H_5$ | —$C_2H_5$ | 71 | $n_D^{26}$:1.4728 |
| 13 | S | —$CH_3$ | —$C_2H_5$ | —$C_2H_5$ | 48 | $n_D^{26}$:1.4859 |
| 14 | S | —$CH_3$ | —C$_6$H$_5$ | —$C_2H_5$ | 60 | $n_D^{26}$:1.5310 |
| 15 | S | —$C_2H_5$ | —$OCH_3$ | —$CH_3$ | 35 | $n_D^{26}$:1.4770 |
| 16 | S | —$C_2H_5$ | —$CH_3$ | —$C_3H_7$-iso | 59 | $n_D^{23}$:1.4783 |
| 17 | S | —$C_2H_5$ | —$C_2H_5$ | —$CH_3$ | 74 | $n_D^{23}$:1.4848 |
| 18 | S | $C_2H_5$ | $C_2H_5$ | $C_4H_9$-iso | 75 | $n_D^{22}$:1.4786 |
| 19 | S | $C_3H_7$-iso | $OCH_3$ | $CH_3$ | 60 | $n_D^{20}$: 1.4720 |
| 20 | S | $C_3H_7$-iso | $CH_3$ | $C_2H_5$ | 75 | $n_D^{20}$: 1.4796 |
| 21 | S | $C_3H_7$-iso | $CH_3$ | $C_3H_7$-iso | 64 | $n_D^{20}$: 1.4750 |
| 22 | S | $C_3H_7$-iso | $C_2H_5$ | $C_3H_7$-n | 57 | $n_D^{20}$: 1.4740 |
| 23 | S | $C_3H_7$-iso | $C_2H_5$ | $C_4H_9$-sec. | 78 | $n_D^{20}$: 1.4747 |
| 24 | S | $C_3H_7$-iso | $CH_3$ | $C_4H_9$-iso | 75 | $n_D^{20}$: 1.4760 |
| 25 | S | $C_2H_5$ | $CH_3$ | $C_2H_5$ | 62 | $n_D^{20}$: 1.4857 |
| 26 | S | $C_2H_5$ | $C_2H_5$ | $C_3H_7$-n | 74 | $n_D^{20}$: 1.4810 |
| 27 | S | $C_2H_5$ | $OC_3H_7$-n | $OC_3H_7$-isoO | 66 | $n_D^{20}$: 1.4685 |
| 28 | O | $C_2H_5$ | $OC_2H_5$ | $C_2H_5$ | 74 | $n_D^{20}$: 1.4525 |
| 29 | S | $CH_3$ | $OCH_3$ | $CH_3$ | 49 | $n_D^{24}$: 1.4823 |
| 30 | S | $CH_3$ | $CH_3$ | $C_2H_5$ | 74 | $n_D^{24}$: 1.4880 |
| 31 | S | $CH_3$ | $CH_3$ | $C_3H_7$-iso | 71 | $n_D^{24}$: 1.4838 |
| 32 | S | $CH_3$ | $CH_3$ | $C_4H_9$-sec. | 71 | $n_D^{24}$: 1.4840 |
| 33 | S | $CH_3$ | $C_2H_5$ | $C_4H_9$-iso | 75 | $n_D^{24}$: 1.4800 |

Other compounds which can be similarly prepared include:

Table 11

| Compound No. | X | R | $R_1$ | $R_2$ |
|---|---|---|---|---|
| 34 | O | —$C_3H_7$-n | —NH-$C_2H_5$ | —$C_3H_7$-iso |
| 35 | S | —$C_4H_9$-iso | —$SC_4H_9$-iso | —$CH_3$ |
| 36 | O | —$CH_3$ | —NH-$C_6H_{13}$-n | —$C_6H_{13}$-n |
| 37 | S | —$C_6H_{13}$-n | —$C_3H_7$-n | —$CH_3$ | and the like.

It will be appreciated that instant specification and examples are set forth by way of illustration and not limitation, and that various modifications and changes may be made without departing from the spirit and scope of the present invention.

What is claimed is:

1. An O-alkyl-O-(1-carbalkoxy-2-tert.-pentyryl-vinyl)-(thiono)(thiol)phosphoric(phosphonic) acid ester or ester-amide of the formula

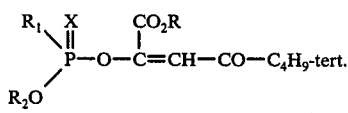

in which
R and $R_2$ each independently is alkyl with 1 to 6 carbon atoms,
$R_1$ is phenyl, or alkyl, alkoxy, alkylthio or alkylamino each with 1 to 6 carbon atoms, and
X is oxygen or sulfur.

2. A method of combating insect or acarid pests which comprises applying to the pests or a habitat thereof an insecticidally or acaricidally effective amount of a compound according to claim 1.

3. The method according to claim 2 in which said compound is
O,O-diethyl-O-(1-carbethoxy-2-tert.-pentyryl-vinyl)-thionophosphoric acid ester,
O-ethyl-O-n-propyl-O-(1-carbisopropoxy-2-tert.-pentyryl-vinyl)-thionophosphoric acid ester,
O-ethyl-O-n-propyl-O-(1-carbethoxy-2-tert.-pentyryl-vinyl)-thionophosphoric acid ester,
O-isopropyl-O-(1-carbethoxy-2-tert.-pentyryl-vinyl)-methanethionophosphonic acid ester, or
O-methyl-O-(1-carbethoxy-2-tert.-pentyryl-vinyl)-ethanethionophosphonic acid ester.

4. An insecticidal or acaricidal composition containing as active ingredient an insecticidally or acaricidally effective amount of a compound according to claim 1 in admixture with a diluent.

5. A compound according to claim 1 in which R and $R_2$ each independently is alkyl with 1 to 4 carbon atoms, $R_1$ is alkyl or alkoxy with 1 to 3 carbon atoms, alkylthio or monoalkylamino with 1 to 4 carbon atoms, or phenyl, and X is sulfur.

6. A compound according to claim 1, wherein such compound is O,O-diethyl-O-(1-carbethoxy-2-tert.-pentyryl-vinyl)-thionophosphoric acid ester of the formula

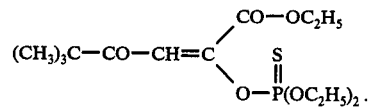

7. A compound according to claim 1, wherein such compound is O-ethyl-O-n-propyl-O-(1-carbisopropoxy-2-tert.-pentyryl-vinyl)-thionophosphoric acid ester of the formula

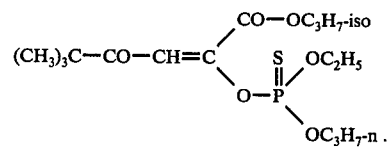

8. A compound according to claim 1, wherein such compound is O-ethyl-O-n-propyl-O-(1carbethoxy-2-tert.-pentyryl-vinyl)-thionophosphoric acid ester of the formula

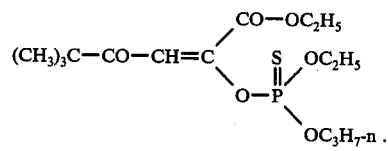

9. A compound according to claim 1, wherein such compound is O-isopropyl-O-(1-carbethoxy-2-tert.-pentyryl-vinyl)-methanethionophosphonic acid ester of the formula

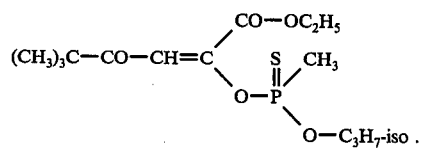

10. A compound according to claim 1, wherein such compound is O-methyl-O-(1-carbethoxy-2-tert.-pentyryl-vinyl)-ethanethionophosphonic acid ester of the formula

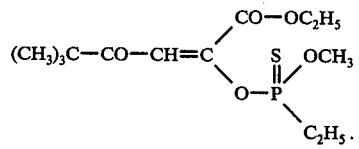

* * * * *